US009506055B2

(12) United States Patent
Lau et al.

(10) Patent No.: US 9,506,055 B2
(45) Date of Patent: *Nov. 29, 2016

(54) REDUCING ADAPTER DIMER FORMATION

(71) Applicant: ILLUMINA, INC., San Diego, CA (US)

(72) Inventors: Patrick Lau, Hayward, CA (US); Danny Lee, Hayward, CA (US)

(73) Assignee: Illumina, Inc., San Diego, CA (US)

( * ) Notice: Subject to any disclaimer, the term of this patent is extended or adjusted under 35 U.S.C. 154(b) by 541 days.

This patent is subject to a terminal disclaimer.

(21) Appl. No.: 14/033,466

(22) Filed: Sep. 22, 2013

(65) Prior Publication Data

US 2014/0018264 A1 Jan. 16, 2014

Related U.S. Application Data

(63) Continuation of application No. 12/952,563, filed on Nov. 23, 2010, now Pat. No. 8,575,071.

(60) Provisional application No. 61/409,867, filed on Nov. 3, 2010.

(51) Int. Cl.
C40B 50/06 (2006.01)
C12N 15/10 (2006.01)
C12Q 1/68 (2006.01)

(52) U.S. Cl.
CPC ......... C12N 15/1068 (2013.01); C12Q 1/6855 (2013.01); C40B 50/06 (2013.01)

(58) Field of Classification Search
None
See application file for complete search history.

(56) References Cited

U.S. PATENT DOCUMENTS 5,754,291 A 5/1998 Kain
5,981,956 A 11/1999 Stern
6,172,218 B1 1/2001 Brenner
6,210,891 B1 4/2001 Nyren et al.
6,258,568 B1 7/2001 Nyren (Continued)

FOREIGN PATENT DOCUMENTS

WO 91/06678 5/1991
WO 98/44151 10/1998

(Continued)

OTHER PUBLICATIONS

Bentley, et al., "Accurate whole human genome sequencing using reversible terminator chemistry", Nature, vol. 456, No. 7218, Nov. 6, 2008, 53-59.

(Continued)

Primary Examiner — Christian Boesen
(74) Attorney, Agent, or Firm — Lisa de Berg; Illumina, Inc.

(57) ABSTRACT

Provided herein is a method of reducing adapter dimer formation comprising contacting a sample comprising target nucleic acid sequences with 5' and 3' adapters in the presence of one or more hairpin oligonucleotides. Also provided is a method of preparing a library of nucleic acid sequences comprising contacting first adapter oligonucleotides with a sample comprising target nucleic acid sequences under conditions to form first ligation products, contacting the sample with one or more hairpin oligonucleotides that binds to the first adapter oligonucleotides, and contacting the sample with second adapter oligonucleotides under conditions to bind to the first ligation products and form second ligation products, wherein the second ligation products form the library of nucleic acid sequences.

16 Claims, 2 Drawing Sheets

(56) References Cited

U.S. PATENT DOCUMENTS

| | | |
|---|---|---|
| 6,274,320 B1 | 8/2001 | Rothberg et al. |
| 6,306,597 B1 | 10/2001 | Macevicz |
| 6,969,488 B2 | 11/2005 | Bridgham et al. |
| 7,057,026 B2 | 6/2006 | Barnes et al. |
| 7,115,400 B1 | 10/2006 | Adessi et al. |
| 7,329,860 B2 | 2/2008 | Feng et al. |
| 7,414,116 B2 | 8/2008 | Milton et al. |
| 7,427,673 B2 | 9/2008 | Balasubramanian et al. |
| 8,575,071 B2 * | 11/2013 | Lau ............... C12Q 1/6855 506/26 |
| 2005/0059048 A1 | 3/2005 | Gunderson et al. |
| 2005/0100900 A1 | 5/2005 | Kawashima et al. |
| 2006/0188901 A1 | 8/2006 | Barnes et al. |
| 2006/0240439 A1 | 10/2006 | Smith et al. |
| 2006/0281109 A1 | 12/2006 | Barr Ost et al. |
| 2007/0031857 A1 | 2/2007 | Makarov et al. |
| 2007/0110638 A1 | 5/2007 | Heiner et al. |
| 2007/0128624 A1 | 6/2007 | Gormley et al. |
| 2007/0166705 A1 | 7/2007 | Milton et al. |
| 2007/0190556 A1 | 8/2007 | Brenner |
| 2009/0011422 A1 | 1/2009 | Devor et al. |
| 2009/0226975 A1 | 9/2009 | Sabot et al. |
| 2010/0062494 A1 | 3/2010 | Church et al. |

FOREIGN PATENT DOCUMENTS

| | | |
|---|---|---|
| WO | 00/18957 | 4/2000 |
| WO | 02/46456 | 6/2002 |
| WO | 2004/018497 | 3/2004 |
| WO | 2004/081183 | 9/2004 |
| WO | 2005/065814 | 7/2005 |
| WO | 2006064199 | 6/2006 |
| WO | 2007/010251 | 1/2007 |
| WO | 2007/123744 | 11/2007 |
| WO | 2008/015396 | 2/2008 |
| WO | 2008/023179 | 2/2008 |

OTHER PUBLICATIONS

Biyani, et al., Nucleic Acids Research vol. 34 article e140, 2006, 1-9.

Iijima, et al., Biochemical and Biophysical Research Communications vol. 350, 2006, 809-817.

Kawano, Mitsuoki et al., "Reduction of non-insert sequence reads by dimer eliminator LNA oligonucleotide for small RNA deep sequencing", Biotechniquest vol. 49, No. 4, Oct. 2010, 751-755.

Morin, et al., Genome Research vol. 18, 2008, 610-621.

Nottrott, et al., The EMBO Journal vol. 18, 1999, 6119-6133.

Ronaghi, M et al., "A Sequencing Method Based on Real-Time Phyrophosphate", Science. Jul. 17, 1998; 281 (5375):363-365 USE, Jul. 17, 1998, 363-365.

Ronaghi, M et al., "Real-time DNA sequencing using detection of pyrophosphate release", Anal. Biochem. Nov. 1, 1996; 242 (1):84-9, Nov. 1, 1996, 84-89.

Ronaghi, Mostafa, "Pyrosequencing sheds light on DNA sequencing", Genome Res, 11(1), 2001, 3-11.

* cited by examiner

SEQUENCE LISTING

<160> NUMBER OF SEQ ID NOS: 25

<210> SEQ ID NO 1
<211> LENGTH: 50
<212> TYPE: RNA
<213> ORGANISM: artificial sequence
<220> FEATURE:
<223> OTHER INFORMATION: Linear Blocker

<400> SEQUENCE: 1
uacgugcaag aguccuacag acggucaucc gggccucacc auacaaucac                50

<210> SEQ ID NO 2
<211> LENGTH: 17
<212> TYPE: RNA
<213> ORGANISM: artificial sequence
<220> FEATURE:
<223> OTHER INFORMATION: Hairpin Blocker 1

<400> SEQUENCE: 2
uuccaacgau ucaacgu                                                    17

<210> SEQ ID NO 3
<211> LENGTH: 15
<212> TYPE: RNA
<213> ORGANISM: artificial sequence
<220> FEATURE:
<223> OTHER INFORMATION: Hairpin Blocker 2

<400> SEQUENCE: 3
uuccaacguu cccgu                                                      15

<210> SEQ ID NO 4
<211> LENGTH: 21
<212> TYPE: RNA
<213> ORGANISM: artificial sequence
<220> FEATURE:
<223> OTHER INFORMATION: Hairpin Blocker 3

<400> SEQUENCE: 4
uuccaccacg auucaacgug g                                               21

<210> SEQ ID NO 5
<211> LENGTH: 22
<212> TYPE: RNA
<213> ORGANISM: artificial sequence
<220> FEATURE:
<223> OTHER INFORMATION: Hairpin Blocker 4

<400> SEQUENCE: 5
gaauuccacc acguucccgu gg                                              22

<210> SEQ ID NO 6
<211> LENGTH: 22
<212> TYPE: DNA
<213> ORGANISM: artificial sequence
<220> FEATURE:
<223> OTHER INFORMATION: Hairpin Chimera Blocker 1
<220> FEATURE:
<221> NAME/KEY: misc_feature
<222> LOCATION: (18)..(22)
<223> OTHER INFORMATION: RNA

<400> SEQUENCE: 6
gaattccacc acgttcccgu gg                                              22

```
<210> SEQ ID NO 7
<211> LENGTH: 21
<212> TYPE: DNA
<213> ORGANISM: artificial sequence
<220> FEATURE:
<223> OTHER INFORMATION: Hairpin Chimera Blocker 2
<220> FEATURE:
<221> NAME/KEY: misc_feature
<222> LOCATION: (17)..(21)
<223> OTHER INFORMATION: RNA

<400> SEQUENCE: 7
ttccaccacg attcaacgug g                                               21

<210> SEQ ID NO 8
<211> LENGTH: 15
<212> TYPE: DNA
<213> ORGANISM: artificial sequence
<220> FEATURE:
<223> OTHER INFORMATION: Hairpin Chimera Blocker 3
<220> FEATURE:
<221> NAME/KEY: misc_feature
<222> LOCATION: (13)..(15)
<223> OTHER INFORMATION: RNA

<400> SEQUENCE: 8
ttccaacgtt cccgu                                                      15

<210> SEQ ID NO 9
<211> LENGTH: 17
<212> TYPE: DNA
<213> ORGANISM: artificial sequence
<220> FEATURE:
<223> OTHER INFORMATION: Hairpin Chimera Blocker 4
<220> FEATURE:
<221> NAME/KEY: misc_feature
<222> LOCATION: (15)..(17)
<223> OTHER INFORMATION: RNA

<400> SEQUENCE: 9
ttccaacgat tcaacgu                                                    17

<210> SEQ ID NO 10
<211> LENGTH: 21
<212> TYPE: DNA
<213> ORGANISM: artificial sequence
<220> FEATURE:
<223> OTHER INFORMATION: Hairpin Chimera Blocker 5
<220> FEATURE:
<221> NAME/KEY: misc_feature
<222> LOCATION: (18)..(21)
<223> OTHER INFORMATION: RNA

<400> SEQUENCE: 10
ttccaccacg attcaacgug g                                               21

<210> SEQ ID NO 11
<211> LENGTH: 22
<212> TYPE: DNA
<213> ORGANISM: artificial sequence
<220> FEATURE:
<223> OTHER INFORMATION: Hairpin Chimera Blocker 6
<220> FEATURE:
<221> NAME/KEY: misc_feature
<222> LOCATION: (20)..(22)
<223> OTHER INFORMATION: RNA

<400> SEQUENCE: 11
gaattccacc acgttcccgu gg                                              22
```

<210> SEQ ID NO 12
<211> LENGTH: 21
<212> TYPE: DNA
<213> ORGANISM: artificial sequence
<220> FEATURE:
<223> OTHER INFORMATION: Hairpin Chimera Blocker 7
<220> FEATURE:
<221> NAME/KEY: misc_feature
<222> LOCATION: (19)..(21)
<223> OTHER INFORMATION: RNA

<400> SEQUENCE: 12
ttccaccacg attcaacgug g                                              21

<210> SEQ ID NO 13
<211> LENGTH: 21
<212> TYPE: DNA
<213> ORGANISM: artificial sequence
<220> FEATURE:
<223> OTHER INFORMATION: 3'-adapter

<400> SEQUENCE: 13
tggaattctc gggtgccaag g                                              21

<210> SEQ ID NO 14
<211> LENGTH: 26
<212> TYPE: RNA
<213> ORGANISM: artificial sequence
<220> FEATURE:
<223> OTHER INFORMATION: 5'-adapter

<400> SEQUENCE: 14
guucagaguu cuacaguccg acgauc                                         26

<210> SEQ ID NO 15
<211> LENGTH: 24
<212> TYPE: RNA
<213> ORGANISM: artificial sequence
<220> FEATURE:
<223> OTHER INFORMATION: Hairpin Blocker 5

<400> SEQUENCE: 15
gaauuccacc acguuuuccc gugg                                           24

<210> SEQ ID NO 16
<211> LENGTH: 24
<212> TYPE: RNA
<213> ORGANISM: artificial sequence
<220> FEATURE:
<223> OTHER INFORMATION: Hairpin Blocker 6

<400> SEQUENCE: 16
gaauuccacc acgucucccc gugg                                           24

<210> SEQ ID NO 17
<211> LENGTH: 24
<212> TYPE: RNA
<213> ORGANISM: artificial sequence
<220> FEATURE:
<223> OTHER INFORMATION: Hairpin Blocker 7

<400> SEQUENCE: 17
gaauuccacc acgucucucc gugg                                           24

<210> SEQ ID NO 18
<211> LENGTH: 24

```
<212> TYPE: RNA
<213> ORGANISM: artificial sequence
<220> FEATURE:
<223> OTHER INFORMATION: Hairpin Blocker 8

<400> SEQUENCE: 18
gaauuccacc acgugugugc gugg                                              24

<210> SEQ ID NO 19
<211> LENGTH: 24
<212> TYPE: RNA
<213> ORGANISM: artificial sequence
<220> FEATURE:
<223> OTHER INFORMATION: Hairpin Blocker 9

<400> SEQUENCE: 19
gaauuccacc acgugugugc gugg                                              24

<210> SEQ ID NO 20
<211> LENGTH: 22
<212> TYPE: RNA
<213> ORGANISM: artificial sequence
<220> FEATURE:
<223> OTHER INFORMATION: Hairpin Blocker 10

<400> SEQUENCE: 20
gaauuccacc acguuucgu gg                                                 22

<210> SEQ ID NO 21
<211> LENGTH: 24
<212> TYPE: RNA
<213> ORGANISM: artificial sequence
<220> FEATURE:
<223> OTHER INFORMATION: Hairpin Blocker 11

<400> SEQUENCE: 21
gagaauucca ccacguuccc gugg                                              24

<210> SEQ ID NO 22
<211> LENGTH: 26
<212> TYPE: RNA
<213> ORGANISM: artificial sequence
<220> FEATURE:
<223> OTHER INFORMATION: Hairpin Blocker 12

<400> SEQUENCE: 22
ccgagaauuc caccacguuc ccgugg                                            26

<210> SEQ ID NO 23
<211> LENGTH: 24
<212> TYPE: RNA
<213> ORGANISM: artificial sequence
<220> FEATURE:
<223> OTHER INFORMATION: Hairpin Blocker 13

<400> SEQUENCE: 23
gaauuccacc acgcuuccgc gugg                                              24

<210> SEQ ID NO 24
<211> LENGTH: 26
<212> TYPE: RNA
<213> ORGANISM: artificial sequence
<220> FEATURE:
<223> OTHER INFORMATION: Hairpin Blocker 14

<400> SEQUENCE: 24
```

```
gaauuccacc acgcguuccc gcgugg                                          26
```

<210> SEQ ID NO 25
<211> LENGTH: 28
<212> TYPE: RNA
<213> ORGANISM: artificial sequence
<220> FEATURE:
<223> OTHER INFORMATION: Hairpin Blocker 15

<400> SEQUENCE: 25

```
acccgagaau uccaccacgu ucccgugg                                        28
```

REDUCING ADAPTER DIMER FORMATION

CROSS-REFERENCE TO RELATED APPLICATION

This application is a continuation of U.S. application Ser. No. 12/952,563, filed Nov. 23, 2010, now U.S. Pat. No. 8,575,071, which claims priority to U.S. Provisional Application No. 61/409,867, filed Nov. 3, 2010, each of which is incorporated by reference herein in its entirety.

BACKGROUND

Methods of creating libraries of nucleic acid molecules for amplification and/or sequencing techniques have been developed. Such methods include adding sequences (e.g., adapters) to the ends of target nucleic acid sequences to facilitate amplification and/or sequencing of the target nucleic acid sequences. For example, adapters that contain primer sequences can be ligated onto the ends of target nucleic acid sequences. A single adapter or two different adapters can be used in the ligation reaction. Such methods are known and described in, for example, WO 98/44151 and WO 00/18957, which are incorporated by reference herein in their entireties. Such methods enable multiple target nucleic acid molecules of the same or different, known or unknown sequence to be amplified in a single amplification reaction. Such target molecules can then be used in, for example, sequencing techniques. However, a drawback in preparing such libraries includes the formation of adapter-dimers.

SUMMARY

Provided herein is a method of reducing adapter dimer formation comprising contacting a sample comprising target nucleic acid sequences with 5' and 3' adapters in the presence of one or more hairpin oligonucleotides under conditions to form 5'-adapter-target-3'-adapter sequences, wherein the amount of adapter dimer formation is reduced compared to the amount of adapter dimer formation in the absence of the hairpin oligonucleotides. Also provided is a method of preparing a library of nucleic acid sequences comprising contacting first adapter oligonucleotides with a sample comprising target nucleic acid sequences under conditions to form first ligation products, contacting the sample with one or more hairpin oligonucleotides that binds to the first adapter oligonucleotides, and contacting the sample with second adapter oligonucleotides under conditions to bind to the first ligation products and form second ligation products, wherein the second ligation products form the library of nucleic acid sequences.

The details of one or more embodiments are set forth in the accompanying drawings and the description below. Other features, objects, and advantages will be apparent from the description and drawings, and from the claims.

DESCRIPTION OF DRAWINGS

As shown in FIG. 1, addition of the 5'-adapter results in adapter dimers and 5'-adapter-target-3'-adapter sequences.

DETAILED DESCRIPTION

Figure 1:
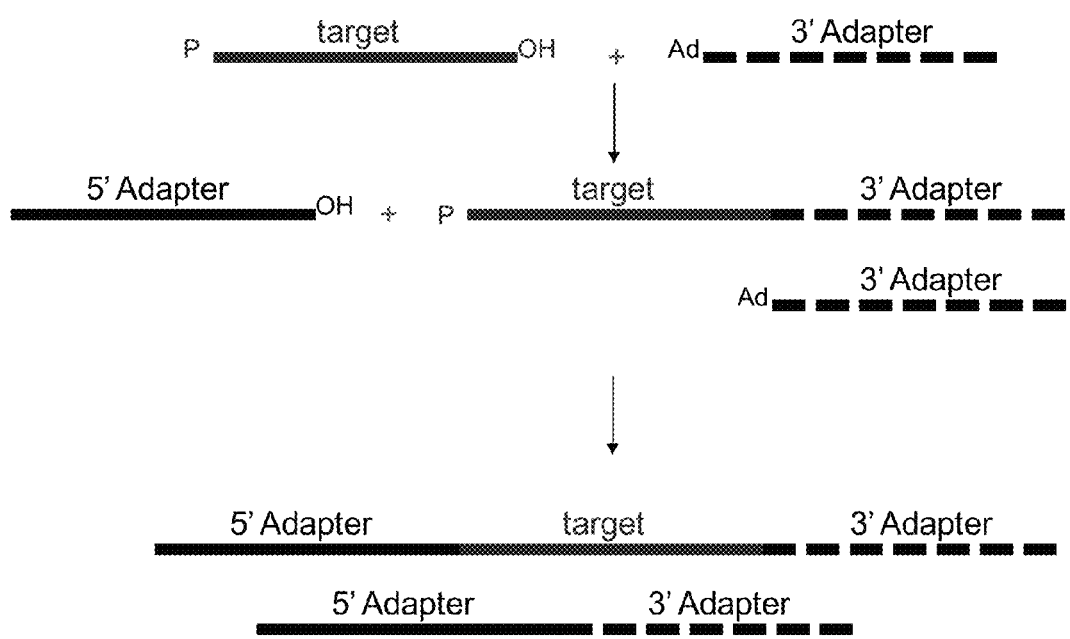
FIG. 1 is a schematic showing adapter dimer formation during ligation of 5'- and 3'-adapters to target nucleic acid sequences. Target nucleic acid sequences are ligated to a 3'-adapter followed by ligation to a 5'-adapter.
Figure 2:
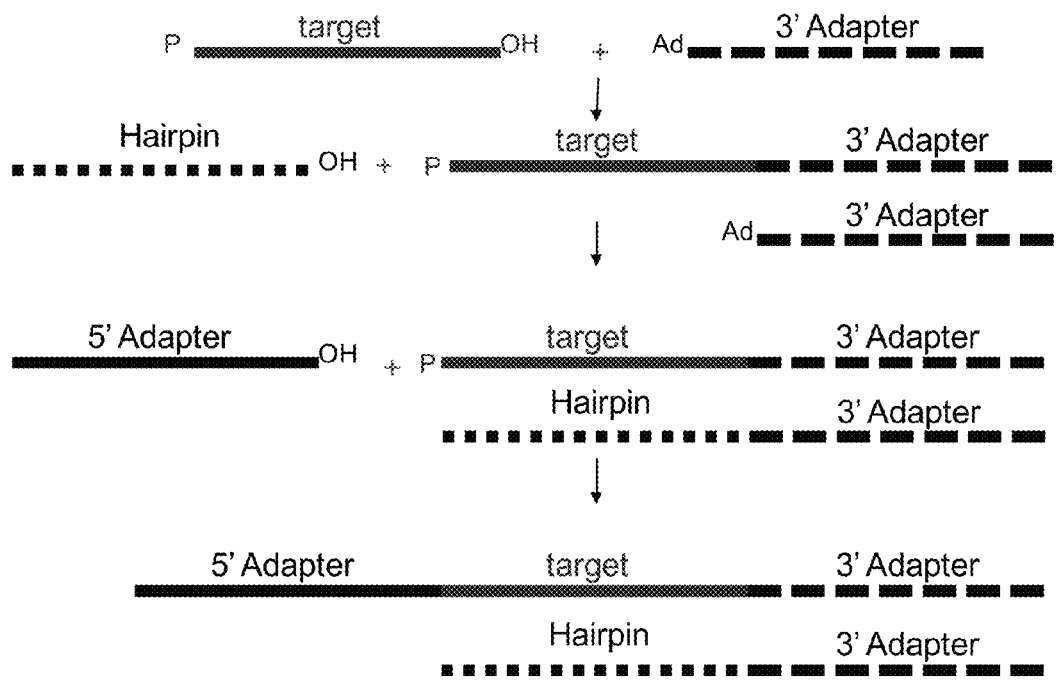
FIG. 2 is a schematic showing reduction of adapter dimer formation using a hairpin oligonucleotide during ligation of 5'- and 3'-adapters to target nucleic acid sequences.
Figure 3:
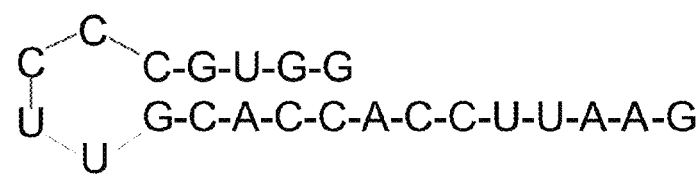
FIG. 3 shows an exemplary hairpin oligonucleotide (SEQ ID NO:5) used in the provided methods.

A major drawback in preparing libraries of target nucleic acids for amplification and/or sequencing by ligating adapters to the ends of the target nucleic acids is the formation of adapter dimers. Adapter dimers are formed by the ligation of two adapters directly to each other such that they do not contain a target nucleic acid insert (i.e., they do not form adapter-target-adapter nucleic acids). See, e.g., FIG. 1. Adapter dimers can reduce the efficiency of amplification reactions since they are generally smaller than the adapter-target-adapter nucleic acids and accumulate at a faster rate. Thus, amplification of the adapter-target-adapter nucleic acids is limited because the components of the amplification reaction, e.g., dNTPs and/or primers, are consumed by the adapter dimers. Similarly, in sequencing techniques, the sequencing of such adapter dimers reduces the efficiency of the technique since the adapter dimers fail to produce useful information as they do not contain target nucleic acids. Thus, preparation of libraries of target nucleic acids with low levels of adapter dimers are desirable, e.g., for amplification and sequencing techniques, including when such processes are high-throughput.

The present application provides methods of reducing adapter dimer formation. For example, the methods relate to preparation of libraries of target nucleic acid sequences in reduced amounts or in the absence of adapter dimers. The present application also provides methods of using such target nucleic acid sequences for amplification and/or sequencing.

The method of reducing adapter dimer formation includes contacting a sample comprising target nucleic acid sequences with 5' and 3' adapters in the presence of one or more hairpin oligonucleotides under conditions to form 5'-adapter-target-3'-adapter sequences, wherein the amount of adapter dimer formation is reduced compared to the amount in the absence of the hairpin oligonucleotides. For example, less than 50, 45, 40, 35, 30, 25, 20, 15, or 10% of the adapters form dimers in the provided methods. Alternatively, at least 50, 55, 60, 65, 70, 75, 80, 85, 90, 95, or 99% of the adapters do not form dimers in the provided methods.

Also provided is a method of preparing a library of nucleic acid sequences. The method includes contacting first adapter oligonucleotides with a sample comprising target nucleic acid sequences under conditions to form first ligation products, contacting the sample with one or more hairpin oligonucleotides that binds to the first adapter oligonucleotides, and contacting the sample with second adapter oligonucleotides under conditions to bind to the first ligation products and form second ligation products, wherein the second ligation products form the library of nucleic acid sequences. In particular embodiments, the 5'-end of the first adapters can be ligated to the 3'-end of the target nucleic acid sequences to form the first ligation products. Optionally, the 3'-end of the second adapters can be ligated to the 5'-ends of the first ligation products to form the second ligation products. Optionally, the target nucleic acid molecules may comprise different sequences.

In the provided methods, ligation of the first adapter to form the first ligation products can occur in the presence of a ligase and in the absence of ATP. This is possible with the use of a pre-adenylated adapter, which is described in more detail below.

The provided methods, optionally, further comprise isolating the second ligation products. Isolation of nucleic acids sequences is known and includes, for example, gel electrophoresis. Suitable, standard methods are also described in, for example, Sambrook and Russell, Molecular Cloning: A Laboratory Manual, Third Edition (2001), which is incorporated by reference herein in its entirety. In particular embodiments, the provided methods further include amplifying and/or sequencing the second ligation products.

As used throughout, oligonucleotides or polynucleotide molecules include deoxyribonucleic acids (DNA), ribonucleic acids (RNA) or other form of nucleic acid. The polynucleotide molecule can be any form of natural, synthetic or modified DNA, including, but not limited to, genomic DNA, copy DNA, complementary DNA, or recombinant DNA. Alternatively, the polynucleotide molecule can be any form of natural, synthetic or modified RNA, including, but not limited to mRNA, ribosomal RNA, microRNA, siRNA or small nucleolar RNA. The polynucleotide molecule can be partially or completely in double-stranded or single-stranded form. The terms "nucleic acid," "nucleic acid molecule," "oligonucleotide," and "polynucleotide" are used interchangeably throughout. The different terms are not intended to denote any particular difference in size, sequence, or other property unless specifically indicated otherwise. For clarity of description the terms may be used to distinguish one species of molecule from another when describing a particular method or composition that includes several molecular species.

As used throughout, the term "target nucleic acid" refers to a nucleic acid molecule to which adapter oligonucleotides are ligated. Target nucleic acid molecules can be any molecule to be amplified or sequenced. Target nucleic acids for use in the provided methods may be obtained from any biological sample using known, routine methods. Suitable biological samples include, but are not limited to, a blood sample, biopsy specimen, tissue explant, organ culture, biological fluid or any other tissue or cell preparation, or fraction or derivative thereof or isolated therefrom. The biological sample can be a primary cell culture or culture adapted cell line including but not limited to genetically engineered cell lines that may contain chromosomally integrated or episomal recombinant nucleic acid sequences, immortalized or immortalizable cell lines, somatic cell hybrid cell lines, differentiated or differentiatable cell lines, transformed cell lines, stem cells, germ cells (e.g. sperm, oocytes), transformed cell lines and the like. For example, polynucleotide molecules may be obtained from primary cells, cell lines, freshly isolated cells or tissues, frozen cells or tissues, paraffin embedded cells or tissues, fixed cells or tissues, and/or laser dissected cells or tissues. Biological samples can be obtained from any subject or biological source including, for example, human or non-human animals, including mammals and non-mammals, vertebrates and invertebrates, and may also be any multicellular organism or single-celled organism such as a eukaryotic (including plants and algae) or prokaryotic organism, archaeon, microorganisms (e.g. bacteria, archaea, fungi, protists, viruses), and aquatic plankton.

The target nucleic acid described herein can be of any length suitable for use in the provided methods. For example, the target nucleic acids can be at least 10, at least 20, at least 30, at least 40, at least 50, at least 75, at least 100, at least 150, at least 200, at least 250, at least 500, or at least 1000 nucleotides in length or longer. Generally, if the target nucleic acid is a small RNA molecule, the target nucleic acid will be at least 10 nucleotides in length. Thus, the target nucleic acid sequences can comprise RNA molecules, for example, small RNA molecules including, but not limited to miRNA molecules, siRNA molecules, tRNA molecules, rRNA molecules, and combinations thereof. In some embodiments, the target nucleic acid sequence comprises single-stranded DNA.

The provided target nucleic acids may be prepared to include 5'- and 3'-adapters using a variety of standard techniques available and known. The adapters can be linear and can be double- or single-stranded. Exemplary methods of polynucleotide molecule preparation include, but are not limited to, those described in Bentley et al., Nature 456:49-51 (2008); WO 2008/023179; U.S. Pat. No. 7,115,400; and U.S. Patent Application Publication Nos. 2007/0128624; 2009/0226975; 2005/0100900; 2005/0059048; 2007/0110638; and 2007/0128624, each of which is herein incorporated by reference in its entirety. Target nucleic acids are modified to comprise one or more regions of known sequence (e.g., an adapter) located on the 5' and 3' ends. Optionally, the adapter comprises the indexing tag. When the target nucleic acid molecules comprise known sequences on the 5' and 3' ends, the known sequences can be the same or different sequences. Optionally, as described more fully below, a known sequence located on the 5' and/or 3' ends of the polynucleotide molecules is capable of hybridizing to one or more oligonucleotides immobilized on a surface. For example, a polynucleotide molecule comprising a 5' known sequence may hybridize to a first plurality of oligonucleotides while the 3' known sequence may hybridize to a second plurality of oligonucleotides.

The adapters that are added to the 5' and/or 3' end of a nucleic acid can comprise a universal sequence. A universal sequence is a region of nucleotide sequence that is common to, i.e., shared by, two or more nucleic acid molecules. Optionally, the two or more nucleic acid molecules also have regions of sequence differences. Thus, for example, the 5' adapters can comprise identical or universal nucleic acid sequences and the 3' adapters can comprise identical or universal sequences. A universal sequence that may be present in different members of a plurality of nucleic acid molecules can allow the replication or amplification of multiple different sequences using a single universal primer that is complementary to the universal sequence. Similarly, at least one, two (e.g., a pair) or more universal sequences that may be present in different members of a collection of nucleic acid molecules can allow the replication or amplification of multiple different sequences using at least one, two (e.g., a pair) or more single universal primers that are complementary to the universal sequences. Thus, a universal primer includes a sequence that can hybridize specifically to such a universal sequence. The target nucleic acid sequence-bearing molecules may be modified to attach universal adapters (e.g., non-target nucleic acid sequences) to one or both ends of the different target nucleic acid sequences, the adapters providing sites for hybridization of universal primers. This approach has the advantage that it is not necessary to design a specific pair of primers for each template to be generated, amplified, sequenced, and/or otherwise analyzed; a single pair of primers can be used for amplification of different templates provided that each template is modified by addition of the same universal primer-binding sequences to its 5' and 3' ends.

In particular embodiments, the 3'-adapter or first adapter oligonucleotide is a 3'-pre-adenylated adapter. Pre-adenylated adapters are known and are described in, for example, U.S. Publication No. 2010/0062494 and U.S. Publication No. 2009/0011422, which are incorporated by reference herein in their entireties. Exemplary 3'-pre-adenylated adapter sequences include, but are not limited to, rAppTGGAATTCTCGGGTGCCAAGG (SEQ ID NO:13) Optionally, the 5'-adapter or second adapter oligonucleotide is a 5'-RNA adapter. Optionally, the 5'-RNA adapter is GUUCAGAGUUCUACAGUCCGACGAUC (SEQ ID NO:14).

As used throughout, the phrases adapter-target-adapter library or library of adapter-target-adapters refers to a collection or plurality of adapter-target-adapter molecules that share common or universal sequences at their 5' ends and common or universal sequences at their 3' ends. The sequences at the 5' and 3' ends of the adapter-target-adapters can be the same or different. Similarly, the target nucleic acid sequences in the adapter-target-adapters can be the same or different.

As used throughout, the term "hairpin oligonucleotide" refers to a nucleic acid sequence that has two complementary regions that hybridize to one another to form a double-stranded region with the two complementary regions being connected by a single-stranded loop. Hairpin oligonucleotides used in the provided methods have additional nucleotides at the 5' end forming a 5' overhanging sequence portion. In particular embodiments, the 5' overhanging sequence portion binds to one of the adapters to reduce or eliminate adapter dimer formation. For example, the single-stranded portion of the hairpin oligonucleotide can anneal to the adapter (e.g., the first or 3'-adapter). Thus, in particular embodiments, the hairpin oligonucleotide is designed such that the 5' overhang sequence is complementary to, at least, a portion of an adapter sequence so that the hairpin can anneal to the adapter. Optionally, the hairpin oligonucleotide is not phosphorylated at its 5'-end such that the hairpin oligonucleotide will not ligate to the second or 5'-adapter. In particular embodiments, the hairpin oligonucleotides are, optionally, not complementary to the target nucleic acid sequences. Exemplary hairpin oligonucleotides that can be used in the provided methods include, but are not limited to SEQ ID NOs: 2-12 and 15-25.

Suitable concentrations of hairpin oligonucleotides for use in the provided methods can be readily determined by those of skill in the art. By way of example, the ratio of hairpin to adapter can be 10:1, 9:1, 8:1, 7:1, 6:1, 5:1, 4:1, 3:1, 2:1 and 1:1. Optionally, the ratio of hairpin to adapter is between 4:1 and 1:1.

The hairpin oligonucleotides described herein can be of any length suitable for use in the provided methods. For example, the hairpin oligonucleodies can be at least 10, at least 20, at least 30, at least 40, or at least 50, nucleotides in length or longer. Optionally, the hairpin oligonucleotides are 15 to 40 base pairs in length.

Optionally, the hairpin and 3'- or first adapter complexes are removed prior to ligation of the 5'- or second adapters to the target-3'-adapter or first ligation products. This can be carried out, for example, by affinity capture. In affinity capture, one member of a binding pair may be attached to hairpin oligonucleotide and the other member of the binding pair can be attached to a surface, e.g., a membrane, column or bead. Thus, the hairpin oligonucleotides may be labeled directly or indirectly. By way of example, the hairpins may be biotinylated (e.g., using enzymatic incorporation of biotinylated nucleotides). Biotinylated hairpin molecules can then be captured on streptavidin-coated beads. Similarly, other hapten-receptor combinations can be used, including, but not limited to, digoxigenin and anti-digoxigenin antibodies or 2,4-dinitrophenol (DNP) and anti-DNP. Fluorogens can also be used to modify the hairpin oligonucleotides. Examples of fluorogens include fluorescein and derivatives, phycoerythrin, allo-phycocyanin, phycocyanin, rhodamine, TEXAS RED® (Molecular Probes, Inc., Eugene, Oreg.) or other fluorogens. The fluorogens are generally attached by chemical modification and bind to a fluorogen-specific antibody, such as anti-fluorescein. It will be understood nucleic acids can also be tagged by incorporation of a modified base containing any chemical group recognizable by specific antibodies. Other tags and methods of tagging nucleotide sequences for capture onto a surface coated with substrate are well known. For example, a review of nucleic acid labels can be found in the article by Landegren, et al. "DNA Diagnostics-Molecular Techniques and Automation", Science, 242:229-237 (1988), which is incorporated herein by reference in its entirety.

As described above, the hairpin oligonucleotides can be labeled and can bind to a surface, including, but not limited to, a column or bead, such as, for example, a magnetic bead. If the label is biotin, the beads (e.g., magnetic beads) are streptavidin-coated beads.

As used herein, a surface includes any solid surface or matrix to which the labeled hairpin oligonucleotide can bind. Suitable solid surfaces or matrices include, for example, beads, resins, gels, wells, columns, chips, flow-cells, membranes, matrices, plates or filters. Solid surfaces can be any solid plastic material in the shape of plates, slides, dishes, beads, particles, cups, strands, chips and strips. Solid surfaces also include glass beads, glass test tubes and any other appropriate glass product.

The target nucleic acid molecules can be modified to include any nucleic acid sequence desirable using standard, known methods. Such additional sequences may include, for example, restriction enzyme sites, or oligonucleotide indexing tag in order to permit identification of amplification products of a given nucleic acid sequence. As described herein, the indexing tag can be added to a polynucleotide molecule by inclusion on an adapter or on a primer. Optionally, the indexing tag can be directly ligated to the ends of a polynucleotide molecule.

Once a library of nucleic acids (e.g., a library of adapter-target-adapters) has been generated, the nucleic acids can be amplified and/or sequenced. Nucleic acid amplification includes the process of amplifying or increasing the numbers of a nucleic acid template and/or of a complement thereof that are present, by producing one or more copies of the template and/or or its complement. Amplification can be carried out by a variety of known methods under conditions including, but not limited to, thermocycling amplification or isotheraml amplification. For example, methods for carrying out amplification are described in U.S. Publication No. 2009/0226975; WO 98/44151; WO 00/18957; WO 02/46456; WO 06/064199; and WO 07/010,251; which are incorporated by reference herein in their entireties. Thus, amplification can occur on the surface to which the nucleic acid molecules are attached. This type of amplification can be referred to as solid phase amplification, which when used in reference to nucleic acids, refers to any nucleic acid amplification reaction carried out on or in association with a surface (e.g., a solid support). For example, all or a portion of the amplified products are synthesized by extension of an immobilized primer. Solid phase amplification reactions are analogous to standard solution phase amplifications except that at least one of the amplification oligonucleotides is immobilized on a surface (e.g., a solid support).

Solid-phase amplification may comprise a nucleic acid amplification reaction comprising only one species of oligonucleotide primer immobilized to a surface. Alternatively, the surface may comprise a plurality of first and second different immobilized oligonucleotide primer species. Solid-phase amplification may comprise a nucleic acid amplification reaction comprising one species of oligonucleotide primer immobilized on a solid surface and a second different oligonucoleotide primer species in solution. Solid phase nucleic acid amplification reactions generally comprise at least one of two different types of nucleic acid amplification, interfacial and surface (or bridge) amplification. For instance, in interfacial amplification, the solid support comprises a template nucleic acid molecule that is indirectly immobilized to the solid support by hybridization to an immobilized oligonucleotide primer, the immobilized primer may be extended in the course of a polymerase-catalyzed, template-directed elongation reaction (e.g., primer extension) to generate an immobilized polynucleotide molecule that remains attached to the solid support. After the extension phase, the nucleic acids (e.g., template and its complementary product) are denatured such that the template nucleic acid molecule is released into solution and made available for hybridization to another immobilized oligonucleotide primer. The template nucleic acid molecule may be made available in 1, 2, 3, 4, 5 or more rounds of primer extension or may be washed out of the reaction after 1, 2, 3, 4, 5 or more rounds of primer extension.

In surface (or bridge) amplification, an immobilized nucleic acid molecule hybridizes to an immobilized oligonucleotide primer. The 3' end of the immobilized nucleic acid molecule provides the template for a polymerase-catalyzed, template-directed elongation reaction (e.g., primer extension) extending from the immobilized oligonucleotide primer. The resulting double-stranded product "bridges" the two primers and both strands are covalently attached to the support. In the next cycle, following denaturation that yields a pair of single strands (the immobilized template and the extended-primer product) immobilized to the solid support, both immobilized strands can serve as templates for new primer extension.

Optionally, amplification of the adapter-target-adapters or library of nucleic acid sequences results in clustered arrays of nucleic acid colonies, analogous to those described in U.S. Pat. No. 7,115,400; U.S. Publication No. 2005/0100900; WO 00/18957; and WO 98/44151, which are incorporated by reference herein in their entireties. Clusters and colonies are used interchangeably and refer to a plurality of copies of a nucleic acid sequence and/or complements thereof attached to a surface. Typically, the cluster comprises a plurality of copies of a nucleic acid sequence and/or complements thereof, attached via their 5' termini to the surface. The copies of nucleic acid sequences making up the clusters may be in a single or double stranded form.

Clusters may be detected, for example, using a suitable imaging means, such as, a confocal imaging device or a charge coupled device (CCD) camera. Exemplary imaging devices include, but are not limited to, those described in U.S. Pat. Nos. 7,329,860; 5,754,291; and 5,981,956; and WO 2007/123744, each of which is herein incorporated by reference in its entirety. The imaging means may be used to determine a reference position in a cluster or in a plurality of clusters on the surface, such as the location, boundary, diameter, area, shape, overlap and/or center of one or a plurality of clusters (and/or of a detectable signal originating therefrom). Such a reference position may be recorded, documented, annotated, converted into an interpretable signal, or the like, to yield meaningful information. The signal may, for instance, take the form of a detectable optical signal emanating from a defined and identifiable location, such as a fluorescent signal, or may be a detectable signal originating from any other detectable label as provided herein. The reference position of a signal generated from two or more clusters may be used to determine the actual physical position on the surface of two clusters that are related by way of being the sites for simultaneous sequence reads from different portions of a common target nucleic acid.

Following amplification, the adapter-target-adapters or library of nucleic acids can be sequenced. The sequencing is carried out by a variety of known methods, including, but not limited to, sequencing by ligation, sequencing by synthesis or sequencing by hybridization.

Sequencing by synthesis, for example, is a technique wherein nucleotides are added successively to a free 3' hydroxyl group, typically provided by annealing of an oligonucleotide primer (e.g., a sequencing primer), resulting in synthesis of a nucleic acid chain in the 5' to 3' direction. These and other sequencing reactions may be conducted on the herein described surfaces bearing nucleic acid clusters. The reactions comprise one or a plurality of sequencing steps, each step comprising determining the nucleotide incorporated into a nucleic acid chain and identifying the position of the incorporated nucleotide on the surface. The nucleotides incorporated into the nucleic acid chain may be described as sequencing nucleotides and may comprise one or more detectable labels. Suitable detectable labels, include, but are not limited to, haptens, radionucleotides, enzymes, fluorescent labels, chemiluminescent labels, and/or chromogenic agents. One method for detecting fluorescently labeled nucleotides comprises using laser light of a wavelength specific for the labeled nucleotides, or the use of other suitable sources of illumination. The fluorescence from the label on the nucleotide may be detected by a CCD camera or other suitable detection means. Suitable instrumentation for recording images of clustered arrays is described in WO 07/123,744, the contents of which are incorporated herein by reference herein in its entirety.

Optionally, cycle sequencing is accomplished by stepwise addition of reversible terminator nucleotides containing, for example, a cleavable or photobleachable dye label as described, for example, in U.S. Pat. Nos. 7,427,673; 7,414,116; WO 04/018497; WO 91/06678; WO 07/123,744; and U.S. Pat. No. 7,057,026, the disclosures of which are incorporated herein by reference in their entireties. The availability of fluorescently-labeled terminators in which both the termination can be reversed and the fluorescent label cleaved facilitates efficient cyclic reversible termination (CRT) sequencing. Polymerases can also be co-engineered to efficiently incorporate and extend from these modified nucleotides.

Alternatively, pyrosequencing techniques may be employed. Pyrosequencing detects the release of inorganic pyrophosphate (PPi) as particular nucleotides are incorporated into the nascent strand (Ronaghi et al., (1996) "Real-time DNA sequencing using detection of pyrophosphate release." *Analytical Biochemistry* 242(1), 84-9; Ronaghi, M. (2001) "Pyrosequencing sheds light on DNA sequencing." *Genome Res.* 11(1), 3-11; Ronaghi, M., Uhlen, M. and Nyren, P. (1998) "A sequencing method based on real-time pyrophosphate." Science 281(5375), 363; U.S. Pat. Nos. 6,210,891; 6,258,568; and 6,274,320, the disclosures of which are incorporated herein by reference in their entireties). In pyrosequencing, released PPi can be detected by being immediately converted to adenosine triphosphate (ATP) by ATP sulfurylase, and the level of ATP generated is detected via luciferase-produced photons.

Additional exemplary sequencing-by-synthesis methods that can be used with the methods described herein include those described in U.S. Patent Publication Nos. 2007/0166705; 2006/0188901; 2006/0240439; 2006/0281109; 2005/0100900; U.S. Pat. No. 7,057,026; WO 05/065814; WO 06/064199; WO 07/010,251, the disclosures of which are incorporated herein by reference in their entireties.

Alternatively, sequencing by ligation techniques are used. Such techniques use DNA ligase to incorporate oligonucleotides and identify the incorporation of such oligonucleotides and are described in U.S. Pat. Nos. 6,969,488; 6,172,218; and 6,306,597; the disclosures of which are incorporated herein by reference in their entireties. Other suitable alternative techniques include, for example, fluorescent in situ sequencing (FISSEQ), and Massively Parallel Signature Sequencing (MPSS).

Also provided are kits for reducing adapter dimer formation including include one or more of the provided hairpin oligonucleotides. The kits can also include 5'- and/or 3'-adapters. Optionally, the kits also include suitable primers of appropriate nucleotide sequence for use with the adapters. The kits may also include buffers, enzymes, such as, for example, a ligase or polymerase, dNTPs, and the like.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation may not be explicitly disclosed, each is specifically contemplated and described herein. For example, if a method is disclosed and discussed and a number of modifications that can be made to the method steps are discussed, each and every combination and permutation of the method steps, and the modifications that are possible are specifically contemplated unless specifically indicated to the contrary. Likewise, any subset or combination of these is also specifically contemplated and disclosed. This concept applies to all aspects of this disclosure. Thus, if there are a variety of additional steps that can be performed it is understood that each of these additional steps can be performed with any specific method steps or combination of method steps of the disclosed methods, and that each such combination or subset of combinations is specifically contemplated and should be considered disclosed.

Throughout this application, various publications are referenced. The disclosures of these publications in their entireties are hereby incorporated by reference into this application.

A number of embodiments have been described. Nevertheless, it will be understood that various modifications may be made. Accordingly, other embodiments are within the scope of the claims.

EXAMPLE

Example 1

Reducing Adapter Dimer Formation Using Hairpin Oligonucleotides

Using total RNA as input, 1 µg of total RNA was added to the first ligation reaction tube containing water and the 3'-pre-adenylated adapter. 5×HM ligation buffer, RNase inhibitor and truncated T4 RNA ligase was then added to the reaction tube and the tube incubated at 28° C. for one hour. The blocker was then added to the reaction tube and incubated at 28° C. for fifteen minutes and then the tube was placed on ice. The 5'-adapter, 10 mM ATP, and T4 RNA ligase was then added to the reaction tube and incubated at 28° C. for one hour. Reverse transcription primer, DTT, 5× First Stand Buffer, 12.5 mM dNTPs, RNase Inhibitor and Superscript II Reverse Transcriptase was added to the reaction tube and incubated at 50° C. for an hour. Ultrapure water, 5×Phusion HF Buffer, 2 PCR primers, Phusion DNA polymerase and 25 mM dNTPs was added to the reaction and the reaction was amplified under the following conditions: 30 seconds at 98° C., 40 cycles of 10 seconds at 98° C., 30 seconds at 60° C., 15 seconds at 72° C., and 10 minutes at 72° C. Following PCR, the products were analyzed for percent adapter dimer formation. The results are shown in Table 1. A variety of blockers were used, an RNA linear blocker (SEQ ID NO:1), four different RNA hairpin blockers (SEQ ID NOs:2-5), and 7 different chimera blockers comprising RNA and DNA sequences (SEQ ID NOs:6-12).

TABLE 1

Percent Adapter Dimer Formation

| Blocker | Concentration (μM) | Percent Adapter Dimer* |
|---|---|---|
| None | 0.0 | 78.9 |
| Linear Blocker (SEQ ID NO: 1) | 1.6 | 81.4 |
| Blocker 1 (SEQ ID NO: 2) | 3.2 | 41.3 |
| Blocker 1 | 6.4 | 41.8 |
| Blocker 2 (SEQ ID NO: 3) | 3.2 | 41.5 |
| Blocker 2 | 6.4 | 39.9 |
| Blocker 3 (SEQ ID NO: 4) | 3.2 | 27.6 |
| Blocker 3 | 6.4 | 17.2 |
| Blocker 4 (SEQ ID NO: 5) | 0.8 | 16.8 |
| Blocker 4 | 1.6 | 17.7 |
| Blocker 4 | 3.2 | 18.8 |
| Blocker 4 | 6.4 | 19.9 |
| Blocker 4 | 12.8 | 23.7 |
| Chimera Blocker 1 (SEQ ID NO: 6) | 3.2 | 87.2 |
| Chimera Blocker 2 (SEQ ID NO: 7) | 3.2 | 90.1 |
| Chimera Blocker 3 (SEQ ID NO: 8) | 3.2 | 22.4 |
| Chimera Blocker 4 (SEQ ID NO: 9) | 3.2 | 16.9 |
| Chimera Blocker 5 (SEQ ID NO: 10) | 3.2 | 58.0 |
| Chimera Blocker 6 (SEQ ID NO: 11) | 3.2 | 13.3 |
| Chimera Blocker 7 (SEQ ID NO: 12) | 3.2 | 58.3 |

*Average of at least two experiments

Sequences:

```
LINEAR BLOCKER (RNA)
                                            SEQ ID NO: 1
UACGUGCAAGAGUCCUACAGACGGUCAUCCGGGCCUCACCAUACAA

UCAC

HAIRPIN BLOCKER 1 (RNA)
                                            SEQ ID NO: 2
UUCCAACGAUUCAACGU

HAIRPIN BLOCKER 2 (RNA)
                                            SEQ ID NO: 3
UUCCAACGUUCCCGU

HAIRPIN BLOCKER 3 (RNA)
                                            SEQ ID NO: 4
UUCCACCACGAUUCAACGUGG

HAIRPIN BLOCKER 4 (RNA)
                                            SEQ ID NO: 5
GAAUUCCACCACGUUCCCGUGG

HAIRPIN CHIMERA BLOCKER 1 (RNA/DNA)
                                            SEQ ID NO: 6
GAATTCCACCACGTTCCrCrGrUrGrG

HAIRPIN CHIMERA BLOCKER 2 (RNA/DNA)
                                            SEQ ID NO: 7
TTCCACCACGATTCAArCrGrUrGrG

HAIRPIN CHIMERA BLOCKER 3 (RNA/DNA)
                                            SEQ ID NO: 8
TTCCAACGTTCCrCrGrU

HAIRPIN CHIMERA BLOCKER 4 (RNA/DNA)
                                            SEQ ID NO: 9
TTCCAACGATTCAArCrGrU

HAIRPIN CHIMERA BLOCKER 5 (RNA/DNA)
                                            SEQ ID NO: 10
TTCCACCACGATTCAACrGrUrGrG

HAIRPIN CHIMERA BLOCKER 6 (RNA/DNA)
                                            SEQ ID NO: 11
GAATTCCACCACGTTCCCGrUrGrG

HAIRPIN CHIMERA BLOCKER 7 (RNA/DNA)
                                            SEQ ID NO: 12
TTCCACCACGATTCAACGrUrGrG

HAIRPIN BLOCKER 5 (RNA)
                                            SEQ ID NO: 15
GAAUUCCACCACGUUUUCCCGUGG

HAIRPIN BLOCKER 6 (RNA)
                                            SEQ ID NO: 16
GAAUUCCACCACGUCUCCCCGUGG

HAIRPIN BLOCKER 7 (RNA)
                                            SEQ ID NO: 17
GAAUUCCACCACGUCUCUCCGUGG

HAIRPIN BLOCKER 8 (RNA)
                                            SEQ ID NO: 18
GAAUUCCACCACGUGUGUGCGUGG

HAIRPIN BLOCKER 9 (RNA)
                                            SEQ ID NO: 19
GAAUUCCACCACGUGUGUGCGUGG

HAIRPIN BLOCKER 10 (RNA)
                                            SEQ ID NO: 20
GAAUUCCACCACGUUUUCGUGG

HAIRPIN BLOCKER 11 (RNA)
                                            SEQ ID NO: 21
GAGAAUUCCACCACGUUCCCGUGG

HAIRPIN BLOCKER 12 (RNA)
                                            SEQ ID NO: 22
CCGAGAAUUCCACCACGUUCCCGUGG

HAIRPIN BLOCKER 13 (RNA)
                                            SEQ ID NO: 23
GAAUUCCACCACGCUUCCGCGUGG

HAIRPIN BLOCKER 14 (RNA)
                                            SEQ ID NO: 24
GAAUUCCACCACGCGUUCCCGCGUGG

HAIRPIN BLOCKER 15 (RNA)
                                            SEQ ID NO: 25
ACCCGAGAAUUCCACCACGUUCCCGUGG
```

What is claimed is:

1. A method of reducing adapter dimer formation comprising:
   (a) contacting first adapter oligonucleotides with a sample comprising target RNA sequences under conditions to form first ligation products;
   (b) after step (a), contacting the sample with one or more hairpin oligonucleotides having a 5' overhang portion configured to bind unligated first adapter oligonucleotides whereby said 5' overhang portion is complementary to and anneals to at least a portion of said unligated first adapter oligonucleotides;
   (c) after step (b), contacting the sample with second adapter oligonucleotides under conditions to bind to the first ligation products and form second ligation products, wherein the second ligation products form the library of nucleic acid sequences, thereby reducing adapter dimer formation.

2. The method of claim 1, wherein step (a) occurs in the presence of a ligase and in the absence of ATP.

3. The method of claim 1, further comprising isolating the second ligation products.

4. The method of claim 3, wherein the isolation comprises gel electrophoresis.

5. The method of claim 1, further comprising amplifying the second ligation products.

6. The method of claim 1, further comprising sequencing the second ligation products.

7. The method of claim 1, wherein the RNA molecules comprise small RNA molecules.

8. The method of claim 7, wherein the small RNA molecules comprise molecules selected from the group consisting of miRNA molecules, siRNA molecules, tRNA molecules, rRNA molecules, and combinations thereof.

9. The method of claim 1, wherein the first adapter is a 3'-pre-adenylated adapter.

10. The method of claim 1, wherein the second adapter is a 5'-RNA adapter.

11. The method of claim 1, wherein the hairpin oligonucleotide comprises RNA.

12. The method of claim 1, wherein the first and second adapters are linear.

13. The method of claim 1, wherein the first and second adapters are single-stranded.

14. The method of claim 1, wherein the hairpin oligonucleotide comprises a label.

15. The method of claim 14, wherein the label binds a column or bead.

16. The method of claim 15, wherein the bead is a magnetic bead.

* * * * *